(12) United States Patent
Lang

(10) Patent No.: US 7,981,858 B1
(45) Date of Patent: Jul. 19, 2011

(54) METHODS OF USING ZINC CONTAINING COMPOUNDS TO IMPROVE OCULAR HEALTH

(75) Inventor: John C. Lang, Cedar Hill, TX (US)

(73) Assignee: Alcon, Inc., Hunenberg (CH)

( * ) Notice: Subject to any disclaimer, the term of this patent is extended or adjusted under 35 U.S.C. 154(b) by 5 days.

(21) Appl. No.: 12/782,057

(22) Filed: May 18, 2010

Related U.S. Application Data

(62) Division of application No. 11/299,582, filed on Dec. 12, 2005.

(60) Provisional application No. 60/638,778, filed on Dec. 22, 2004.

(51) Int. Cl.
*A61K 38/00* (2006.01)
*A61K 51/00* (2006.01)
*A61K 38/06* (2006.01)

(52) U.S. Cl. ........ 514/1.1; 424/1.69; 530/331; 514/15.1

(58) Field of Classification Search .................. None
See application file for complete search history.

(56) References Cited

U.S. PATENT DOCUMENTS

| | | | |
|---|---|---|---|
| 3,998,753 A | 12/1976 | Antoshkiw et al. | |
| 4,254,100 A | 3/1981 | Keller et al. | |
| 4,670,247 A | 6/1987 | Scialpi | |
| 5,156,852 A | 10/1992 | LaHaye et al. | |
| 6,573,299 B1 | 6/2003 | Petrus | |
| 6,582,721 B1 | 6/2003 | Lang | |
| 6,586,611 B1 * | 7/2003 | Newsome et al. | 556/134 |
| 6,716,447 B1 | 4/2004 | Lang | |
| 2006/0134226 A1 | 6/2006 | Leonard | |

OTHER PUBLICATIONS

Alexander et al. Acta Pharmacol Toxicol (Copenh). Sep. 1981;49(3):190-4).*
Bae et al. Characteristics of glutathione-capped ZnS nanocrystallites. Biochemical and Biophysical Research Communications. vol. 237, Issue 1, Aug. 8, 1997, pp. 16-23.*
Nishimura et al. L-carnosine and close derivatives accelerate zinc update from the intestine in rats. Biomed Res. Trace Elements, 12(2): 159:167, 2001 (Table 5, GSH-Zn).*
Alexander et al.; "Excretion of zinc in rat bile—a role of glutathione"; Acta Pharmacol., et. Toxicol.; vol. 49; pp. 190-194 (1981).
Fur and Rabenstein; "Nuclear magnetic resonance studies of the solution chemistry of metal complexes. IX. The binding of cadmium, zinc, lead, and mercury by glutathione"; Journal of the American Chemical Society; vol. 95; No. 21; pp. 6944-6950 (Oct. 17, 1973).
Li et al.; "Stability of zinc complexes with glutathione and oxidized glutathione"; JACS; vol. 76; pp. 225-229; (Jan. 5, 1954).
Newsome et al.; "Oral zinc in macular degeneration"; Arch. Ophthalmol. vol. 106; pp. 192-198 (Feb. 1988).
Nishimura et al; "L-carnosine and close derivatives accelerate zinc uptake form the intestine in rats"; Biomed. Res. Trace Elements; vol. 12; No. 2; pp. 159-167 (2001).
Perrin and Watt; "Complex formation of zinc and cadmium with glutathione"; Biochim. Biophys. Acta; vol. 230; pp. 96-104 (1971).
Sato et al; "The distribution and binding of zinc in the hippocampus"; The Journal of Neuroscience; vol. 4; No. 6; pp. 1662-1670 (Jun. 1984).
Sato et al; "A kinetic study of the in vivo incorporation of 65ZN into the rat hippocampus"; The Journal of Neuroscience; vol. 4; No. 6; pp. 1671-1675 (Jun. 1984).

* cited by examiner

*Primary Examiner* — Maury Audet
(74) *Attorney, Agent, or Firm* — Teresa J. Schultz

(57) ABSTRACT

The present invention provides zinc complexes for use in methods of providing zinc to subjects in need of treatment. The invention further provides improved dietary supplement formulations for improving and maintaining ocular nutrition. In particular, the improved dietary supplement formulations comprise the zinc complexes described herein, antioxidant vitamins, minerals and excipients.

9 Claims, No Drawings

METHODS OF USING ZINC CONTAINING COMPOUNDS TO IMPROVE OCULAR HEALTH

This application is a divisional of U.S. patent application Ser. No. 11/299,582, filed Dec. 12, 2005, which claims priority from provisional application, U.S. Patent Application Ser. No. 60/638,778 filed Dec. 22, 2004.

BACKGROUND OF THE INVENTION

1. Field of the Invention

The present invention relates to the field of nutraceuticals and to the use of dietary supplements to maintain or improve ocular health.

2. Description of the Related Art

Dietary supplements are recommended for a variety of reasons including the improvement of vision or prophylaxis of vision loss. An example of dietary supplements useful in improving ocular nutrition and promoting healthy eyes are the ICaps® Dietary Supplements (Alcon Laboratories, Inc., Fort Worth, Tex.). Dietary supplements are generally consumed in the form of powders, tablets, capsules or gel-caps and comprise a variety of vitamins, minerals, and herbal or other organic constituents. Some dietary supplements are formulated with beadlets, which may function as carriers for the nutritional ingredients and may be blended and compressed into tablets or filled into capsules or gel caps.

Zinc, an essential nutrient, is the second most abundant trace element in the human body and the most abundant trace element in the eye. It is necessary for the activity of more than 200 enzymes and for the DNA binding capacity of over 400 nuclear regulatory elements. There is evidence that zinc may function as an antioxidant by protecting sulfhydryl groups from oxidation, competing with copper and iron to reduce the formation of hydroxyl radicals which are a result of redox cycling and by the induction of the antioxidant protein metallothionein (MT) which can scavenge damaging hydroxyls.

It has been suggested that oxidative stress and a decrease in anitoxidant capacity play a role in several pathological conditions such as atherosclerosis, carcinogenesis, and macular degeneration. Age-related macular degeneration (AMD) is the number one cause of blindness in people over 60 in the United States. It is thought that it is an age-related defect in the retinal pigment epithelium (RPE) which contributes to this disease, however, the etiology is unknown and currently there is no cure.

Zinc is an important micronutrient that plays an essential role in human growth and function. Zinc is necessary for the activity of over a hundred enzymes, including carbonic anhydrase, superoxide dismutase and alkaline phosphatase. Zinc acts as a cofactor for numerous metalloenzymes, including retinol dehydrogenase and catalase. Zinc also is a cofactor in the synthesis of extracellular matrix molecules, is essential for cell membrane stability, is needed for normal immune function, is associated with melanin and is taken up in a facilitated manner by the retinal pigment epithelium.

U.S. Pat. No. 6,586,611 describes a molecular structure for a zinc monocysteine complex. The '611 patent provides only one structure for the zinc monocysteine complex described and does not describe other zinc complexes. What is needed is a more bioavailable form of zinc, in a form other than the zinc monocysteine complex previously described, in order for it to be more effective for use in dietary supplements for the improvement of ocular health.

SUMMARY OF THE INVENTION

The present invention overcomes these and other drawbacks of the prior art by providing zinc containing compounds, other than zinc cysteine, that are bioavailable and beneficial to ocular health. In that respect, the present invention provides zinc containing structures having the formula:

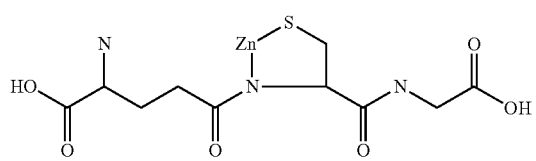

The present invention is also directed to improved dietary supplements comprising the zinc complexes of the invention. Preferred dietary supplements are formulated as an aid to ocular health. The present invention is also directed to methods of using the zinc complexes and dietary supplements for improving nutritional health. The methods of the present invention are particularly directed to the enhancement of ocular health and the prophylaxis of retinal disorders, including age-related macular degeneration.

Newsome (U.S. Pat. No. 6,586,611) describes zinc-mono cysteine complexes having a six-membered ring structure. The present inventor has discovered that the five-membered ring structure represented above is more stable and useful for delivering zinc and other important agents to the eye for improving ocular health. For example, transporting the glutathione molecule with zinc as part of the agent of the invention, would transport a more active compound (glutathione) to the eye. Glutathione is known to be directly involved in control of the oxidative of ocular cells, particularly retina cells. Delivering cysteine to the ocular cells, on the other hand, would require the ocular cells to under further biosynthesis to generate glutathione.

It is further contemplated that zinc complexes containing zinc and other amino acids, oligo- or polypeptides having free or accessible nitrogen and sulfur atoms. Such complexes could be used either to deliver the zinc or the other molecular component of the complex to ocular tissues. It is further contemplated that long-chain alcohols could be incorporated into the complexes of the invention as the mono or diester of the fatty acid fraction of the zinc complex. If the long chain alcohol were a glycol, the glycol would serve as a bridge between two peptide units, each containing zinc. An example of a structure of benefit to the eye would be a xanthophyll, like lutein or zeaxanthin.

The zinc-glutathione complex of the invention can be administered orally, and the amount administered is preferably 15-100 mg bioavailable zinc. The present invention also provides a method of providing glutathione, or other amino acids, oligo-, or polypeptides to a subject in need of treatment by administering to the subject an effective amount of a zinc complex as described herein.

It will be understood by the skilled artisan that the percentage ranges above (i.e., 0.1% to 50%, etc.) include all points in between said range. That is, it includes 0.2%, 0.3%, 0.4% and so on, 1.0%, 1.1%, 1.2% and so on, 5.0%, 5.1%, 5.2% ... 5.7%, 5.8%, 5.9% and so on up to and including 20%, 25%, 30%, 40%, etc.

The dietary supplements of the invention may comprise additional ocular health-enhancing substances, such as antioxidants, vitamins and minerals. Preferred substances for inclusion in the dietary supplements of the invention include, but are not limited to, Vitamin A, Vitamin C, Vitamin E, rosemary, DHA, zinc, zinc complexes, copper, and selenium. Some of the ingredients in the dietary supplements may be encapsulated in beadlets, providing additional stability of the supplements and bioavailability of the active ingredients. Preferred beadlets for use in the supplements of the invention are described in U.S. Pat. Nos. 6,582,721 and 6,716,447, incorporated herein by reference.

The beadlets for use in the supplements of the invention may be in the form of capsular reservoir or monolithic matrix. Capsular reservoirs for an oily active, such as those of the current invention, typically consist of at least one surface-active agent, such as phospholipids and water-soluble polymers, utilized to stabilize microparticles of the active agent(s) suspended in a medium in which they do not dissolve. The coating may be any film-forming type of coating material, such as carbohydrates (acacia and cellulose is derivatives and dextrans to gelatin), gluten, polyesters, starch, lactide-glycolide copolymers, waxes, etc. One of skill in the art may easily select appropriate coatings based on their properties and their compatibility with the active component(s) and selected/required excipients.

Monolithic matrices essentially trap the active agent(s) within a "web" of polymer. While the monolithic matrix may be formed using any known method, it will generally be formed by precipitation polymerization, coacervation of polymeric blends, condensation polymerization, or by simple drying. In certain embodiments, the core of the carrier may comprise a monolithic matrix while the remainder of the beadlet is a capsular reservoir. In a preferred aspect, the core may be generated with acrylates.

The matrix may be loaded with active agent(s) either before or after polymerization. Whether loading occurs before or after polymerization will depend on the nature of the active agent(s) and/or upon the capacity of the carrier. Such determinations are well within the knowledge and the skill of the ordinary skilled artisan.

In addition, either type of microparticle may require other excipients such as plasticizers, dispersants, colorants and/or opaquants, extenders, and fillers.

Further, where the active agent(s) are unstable it may be further desirable to combine the capsular reservoir and matrix technologies. That is, the active agent(s) may be embedded within a matrix and then the matrix coated to restrict transport of degradizer into the core. This embodiment is preferred where one or more of the active agents are antioxidants. In certain preferred aspects, protective antioxidants can be placed in the core to protect the most vulnerable specie, and may also be placed in the coating. Such a coating can serve two purposes: first, the coating isolates the active and may reduce the rate at to which reactive oxygen reaches the active embedded in the core; and second, the antioxidant in the coating serves to reduce the limited amount of oxygen in the head space of the container, generally a plastic bottle of tablets or capsules.

The present invention further provides a method of maintaining or improving ocular health in a mammal. The method of the invention generally includes administering to a mammal a composition comprising the zinc complex of the invention, along with other ingredients useful for the promotion of ocular health, such as Vitamin A, in the form of β-carotene, Vitamin C, Vitamin E, and copper. Additional embodiments may further include DHA and/or rosemary. In preferred embodiments, the dietary supplements for use in the methods of the invention will be as described above. Typically, the composition for use in the methods of the invention can be administered in many forms, including powder, capsule, caplet, gel cap or tablet. Most preferably, the composition will be administered in the form of a tablet, a tablet also intended to deliver other micronutrients of value in maintaining ocular nutrition.

DETAILED DESCRIPTION PREFERRED EMBODIMENTS

The present invention is directed to improved zinc formulations, improved dietary supplement formulations comprising the improved zinc formulations and methods of use. As used herein, "dietary supplement(s)" or the shortened form, "supplement(s)," refer to any finished, dietary supplement dosage form containing dietary substances and suitable for ingestion by a host, e.g., human or other mammal.

Zinc is important in maintaining the health of an eye's retina and is an essential part of more than 100 enzymes involved in digestion, metabolism, reproduction and wound healing. The recommended dietary allowance for zinc is approximately 15 mg. In one study, 80 mg of zinc was shown to be significantly better than placebo in retarding macular degeneration changes. (Newsome, *Arch. Ophthalm.* 106:192-198 (1988)). About 200 mg dosage of zinc per day, although well tolerated, has been shown to have potential side effects such as anemia. The anemia associated with high dosage zinc intake is attributable is to copper deficiency. Diet supplementation with copper does not appear to have a deleterious effect on zinc absorption. Accordingly, preferably the dietary supplements of the invention provide zinc in the form of the zinc complexes described herein, as well as approximately 0.4 mg to 4 mg of copper.

It was known that including antioxidants safe for human consumption, such as tocopherols (vitamin E-related compounds) and ascorbates (vitamin C derivatives), in beadlets with lutein protected the lutein from oxidation. Without being bound to any theory, it is believed that the antioxidants protect the lutein by behaving in specific ways: (1) all of the oxygen in the head space eventually reacts with antioxidants; (2) any oxygen which diffuses through the plastic bottle also will react with the confined antioxidants; (3) the oxygen reacts more rapidly with the most oxidizable antioxidants. Thus, the antioxidants in the beadlets are "used up" before oxidization can effect the more important active ingredient. While the DHA has been found to be protected by the rapidly oxidizable components in rosemary, other sources of even more rapidly oxidizable concentrated botanically derived antioxidant are anticipated to provide comparable benefit and are envisioned to be encompassed by the claimed technology.

Some antioxidants, namely vitamins C and E and rosemary, are effective in protecting retinas from acute light-induced toxicity. Cellular antioxidants function in a cascade of reactions in order to protect sensitive organelles against reactive oxygen species to in metabolizing tissues, in which oxygen eventually is reduced to water. For example, ascorbate is known to regenerate the reduced specie of Vitamin E from the oxidized specie. Therefore, including rosemary in sufficient quantities in a co-beadlet with DHA in the dietary supplements of the invention might serve multiple purposes. First, it acts as a second active ingredient, providing protection for the eyes and improving ocular health. Second, it acts as a "stabilizer," increasing shelf-life of the product. Finally, it acts as a "de-odorizer," masking the marine-odor of the DHA by preventing its oxidation, and imparting a favorably perceived fragrance.

It is contemplated that virtually any beadlet technology, such as that described in U.S. Pat. Nos. 4,254,100; 3,998,753; 4,670,247; and 3,998,753 will be useful in the practice of the present invention for embodiments containing antioxidants and other components in addition to the zinc complexes of the invention.

The present invention additionally provides a composition of the dosage form, containing the zinc complexes described herein, along with other antioxidants (which may or may not be confined in beadlets)

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A. Actives & Excipients (Indented) in an Ophthalmic Formulation

Ascorbic Acid
  Gelatin
  Hydroxypropyl Methylcellulose
dl-Alpha Tocopherol Acetate
  Dicalcium Phosphate
  Microcrystalline Cellulose
  Magnesium Stearate
  Sucrose
  Silicon Dioxide
Zinc Complex
Manganese Amino Acid Chelate
  Corn Starch
  Water
  Sodium alginate
Selenium Amino Acid Chelate
  Soy protein (isolated)
  Titanium Dioxide
  Hydroxypropyl cellulose (Klucel)
  Fatty acids (DHA excipients)
DHA (in oil carrier)
Copper Amino Acid Chelate
Riboflavin
  Polyethylene Glycol
Lutein/Zeaxanthin
  Water and Ca
  Ethoxylated glycerides
  Ascorbyl Palmitate
Beta Carotene
Rosemary (from Herbalox type O)
  Sodium Ascorbate
  dl-Alpha Tocopherol
Zeaxanthin
  Canola oil (Herbalox excipient)
  Soybean oil (Herbalox excipient)
  Excipients
  Sorbic Acid
  Polysorbate 80
  Sodium Benzoate
Folic Acid
  Vegetable oil (Lyc-o-Rose excipient)
  Carnauba Wax
Cyanocobalamin All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and structurally related may be substituted for the agents described herein to achieve similar results. All such substitutions and modifications apparent to those skilled in the art are deemed to be within the spirit, scope and concept of the invention as defined by the appended claims.

REFERENCES

The references cited herein, to the extent that they provide exemplary procedural or other details supplementary to those set forth herein, are specifically incorporated herein by reference.

I claim:

1. A method of providing zinc to a subject suffering from or at risk for developing macular degeneration, said method comprising administering to the subject an effective amount of a composition comprising a zinc-glutathione complex having the formula

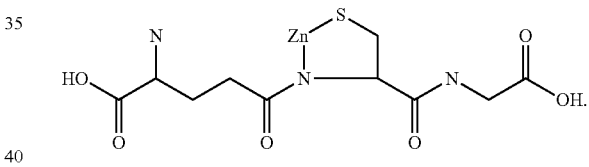

2. The method of claim 1, wherein the amount of zinc-glutathione complex contained in the composition contains from 15 to 100 mg bioavailable zinc.

3. The method of claim 1, wherein the composition further comprises vitamin A, vitamin C, vitamin E and copper.

4. The method of claim 3, wherein the composition further comprises docosahexaenoic acid (DHA).

5. The method of claim 1, wherein the composition is in a form selected from the group consisting of a powder, capsule, caplet, gel cap, and tablet.

6. The method of claim 5, wherein the composition is a tablet.

7. The method of claim 1, wherein the composition further comprises copper.

8. The method of claim 7, wherein the amount of copper in the composition is from about 0.4 mg to about 4 mg.

9. The method of claim 8, wherein the amount of zinc-glutathione complex in the composition is about 80 mg.

* * * * *